United States Patent
Chou et al.

(10) Patent No.: US 10,555,886 B2
(45) Date of Patent: Feb. 11, 2020

(54) COMPOSITION OF ALGAL EXTRACTS FOR PREVENTING AND TREATING PERIODONTAL DISEASE

(71) Applicant: Far East Bio-Tec. Co., Ltd., Taipei (TW)

(72) Inventors: Tz-Chong Chou, Taipei (TW); Chuang-Chun Chiuh, Taipei (TW)

(73) Assignee: FAR EAST BIO-TEC CO., LTD., Taipei (TW)

( * ) Notice: Subject to any disclaimer, the term of this patent is extended or adjusted under 35 U.S.C. 154(b) by 387 days.

(21) Appl. No.: 14/729,743

(22) Filed: Jun. 3, 2015

(65) Prior Publication Data

US 2016/0354298 A1 Dec. 8, 2016

(51) Int. Cl.
 *A61K 35/748* (2015.01)
 *A61K 8/64* (2006.01)
 *A61Q 11/00* (2006.01)

(52) U.S. Cl.
 CPC ............ *A61K 8/64* (2013.01); *A61Q 11/00* (2013.01); *A23V 2002/00* (2013.01); *A61K 2800/74* (2013.01)

(58) Field of Classification Search
 CPC ........ A61K 36/02; A61K 36/03; A61K 36/04; A61K 36/05
 See application file for complete search history.

(56) References Cited

U.S. PATENT DOCUMENTS

| | | | | |
|---|---|---|---|---|
| 2007/0134813 A1* | 6/2007 | Boga | ...... | G01N 33/558 436/518 |
| 2010/0196288 A9* | 8/2010 | Kim | ...... | A61K 36/07 424/58 |
| 2011/0165279 A1* | 7/2011 | Lin | ...... | A61K 36/39 424/773 |
| 2012/0088204 A1* | 4/2012 | Ho | ...... | A61N 5/0603 433/29 |
| 2013/0266522 A1* | 10/2013 | Fagon | ...... | A61K 33/08 424/50 |
| 2013/0323683 A1* | 12/2013 | Piergallini | ...... | A61N 5/062 433/215 |

FOREIGN PATENT DOCUMENTS

JP 2009062339 A * 3/2009

OTHER PUBLICATIONS

Mahendra et al. J. Clin. Diag. Res. 2013. vol. 7, No. 10, pp. 2330-2333.*
Gur et al. J. Med. Plants Res. 2013. vol. 7, No. 8, pp. 425-433.*
Reddy et al. Biochem. Biophys. Res. Com. 2000. vol. 277, pp. 599-603.*
Beresescu et al. Eur. Sci. J. 2014. vol. 10, No. 36, pp. 142-147.*
Taufiqurrahmi et al. 29th Symposium of Malaysian Chemical Engineers. 2016. pp. 1-6.*

* cited by examiner

Primary Examiner — Ralph J Gitomer
(74) Attorney, Agent, or Firm — Muncy, Geissler, Olds & Lowe, P.C.

(57) ABSTRACT

A composition of algal extracts containing phycobiliprotein is provided. This composition not only effectively inhibit the growth of oral pathogens including *Porphyromonathes gingivalis* and *Actinobacillus actinomycetemcomitans*, but also reduces the inflammation caused by those pathogens. Therefore, the phenomenon of alveolar bone loss in periodontal patients is mitigation, achieving the effect of prevention and treatment of periodontal disease.

12 Claims, 8 Drawing Sheets

COMPOSITION OF ALGAL EXTRACTS FOR PREVENTING AND TREATING PERIODONTAL DISEASE

FIELD OF THE INVENTION

The present invention relates to a new use of the phycocyanin extracts, it can effectively inhibit the growth of the oral pathogens, improve the alveolar bone loss situation and reduce the inflammation caused by those pathogens. More particularly, the present invention of the phycocyanin extracts can treat and/or prevent of periodontal disease.

BACKGROUND OF THE INVENTION

Periodontal disease is a kind of the chronic disease, occurs at a high frequency throughout the world. According to the statistics of Taiwan Academy of Periodontology, over 90 percents of adults have gum disease in Taiwan. These patients might have ugly teeth, bad breath and suffer from other oral diseases. Moreover, it seriously affects the interpersonal relationships with others during social activities. The main factor of periodontal disease is the growth of the oral pathogens, others include smoking, genetic, stress, diet, age, diabetes, osteoporosis, HIV infection, radiation exposure and administration of drugs that suppress the immune ability and so on. These factors are likely to increase the risk of suffering from periodontal disease and also exacerbate the damages done by those pathogens.

In between gums and teeth is a groove and the groove is called the gingival sulcus. Result of poor oral hygiene, the oral pathogens would grow in the gingival sulcus and gradually to form a biofilm. These main oral pathogens are *Porphyromonas gingivalis* and *Actinobacillus actinomycetemcomitans*. These oral pathogens adhere and aggregate to the biofilm to form a plaque.

The oral pathogens within the plaque will invade the surrounding gum tissue, and gradually form a periodontal pocket. The invaded oral pathogens itself and its secreted toxins will induce the pro-inflammatory factors, including cyclooxygenase (COX) products and inducible NO synthase (iNOS) metabolites, etc. These factors will directly or indirectly cause damage to the surrounding gum tissue.

In clinical practice, it is very important to observe the height of periodontal alveolar bone in patients. Because the height of the alveolar bone will directly affect the holding of the teeth. The density of bone within our body is the result of constant interaction between deposition and resorption. When the rate of the deposition is faster than the rate of resorption, the internal bone is increased. If the rate of the resorption is faster than the rate of deposition, the internal bone is decreased. Periodontal alveolar bone works the same mechanism. The deposition and the resorption of bone depends on the osteoblasts and the osteoclast. When the pathogens enter the alveolar bone, the pathogens will destroy the capillary blood vessels, block the supply of the nutrients and reduce the osteoblast activity. On the other hand, the inflammatory factors (e.g., TNF-α, IL-1) and immune cells (e.g. T cells) induced by the pathogens, increase the osteoclasts activity tremendously. These situations cause alveolar bone atrophy and bone loss, further leads to exposure of teeth root and loss of teeth In summary, the pathogens in the plaque is the main reason of the periodontal disease. Thus reducing the accumulation and proliferation of these pathogens are the primary goal of prevention and treatment of periodontal disease. In clinical, the main cure method of the periodontal disease is through surgical treatment to clear of the plaque. Currently, there is no efficienct drug therapy for the periodontal disease. Therefore the drug therapy is a very important field for further research and development.

SUMMARY OF THE INVENTION

The present invention provides a composition for treating the periodontal disease comprising an effective concentration of a phycobiliprotein.

The present invention provides a composition for preventing the periodontal disease comprising an effective concentration of a phycobiliprotein.

In some embodiments, the effective concentration is great than 50 µg/ml, and the best concentration is between 50 µg/ml~600 µg/ml.

In some embodiments, the treatment and/or prevention of periodontal disease is through inhibit the growth of the oral pathogens, the growth of oral pathogens include *Porphyromonas gingivalis* and *Actinobacillus actinomycetemcomitans*.

In some embodiments, the treatment and/or prevention of periodontal disease is to effectively reduce alveolar bone loss in patients.

In some embodiments, the treatment and/or prevent of periodontal disease is to effectively reduce the inflammation caused by those pathogens in patients.

In some embodiments, the phycocyanin is select from the group consist of phycocyanin, phycoerythrin and allophycocyanin.

In some embodiments, the phycocyanin is C-phycocyanin.

In some embodiments, the composition can be made into a paste, an injection or a patch.

In some embodiments, the composition can add to oral hygienic products, such as toothpaste, powder, mouthwash or dental floss.

In some embodiments, the composition can be applied in the orthodontic tools, such as braces or dentures In some embodiments, the composition can be applied in the braces or dentures, such as adhesive or denture cleaning solution.

In some embodiments, the composition can be applied in the dental materials, such as silver amalgam and synthetic resins.

In some embodiments, the composition can be mixed in chewing gum, fresh mint tablets or other mouth freshener.

In some embodiments, the composition further combine with other pharmaceutically acceptable excipient.

In some embodiments, the composition further can be a food additive.

The details of one or more embodiments of the invention are set forth in the description below. Other features or advantages of the present invention will be apparent from the following detailed description of an example and also from the appended claims.

DETAILED DESCRIPTION OF THE INVENTION

Embodiment 1

The Antimicrobial Test

1. Culture of the Pathogens

According to the experiment process of the reference paper Jeong et al., 2000 and Zhou et al., 2006, the main pathogens of the periodontal disease *Porphyromonas gingivalis* and *Actinobacillus actinomycetemcomitans* are cultured.

2. The Antimicrobial Experiment

Figure 1A:
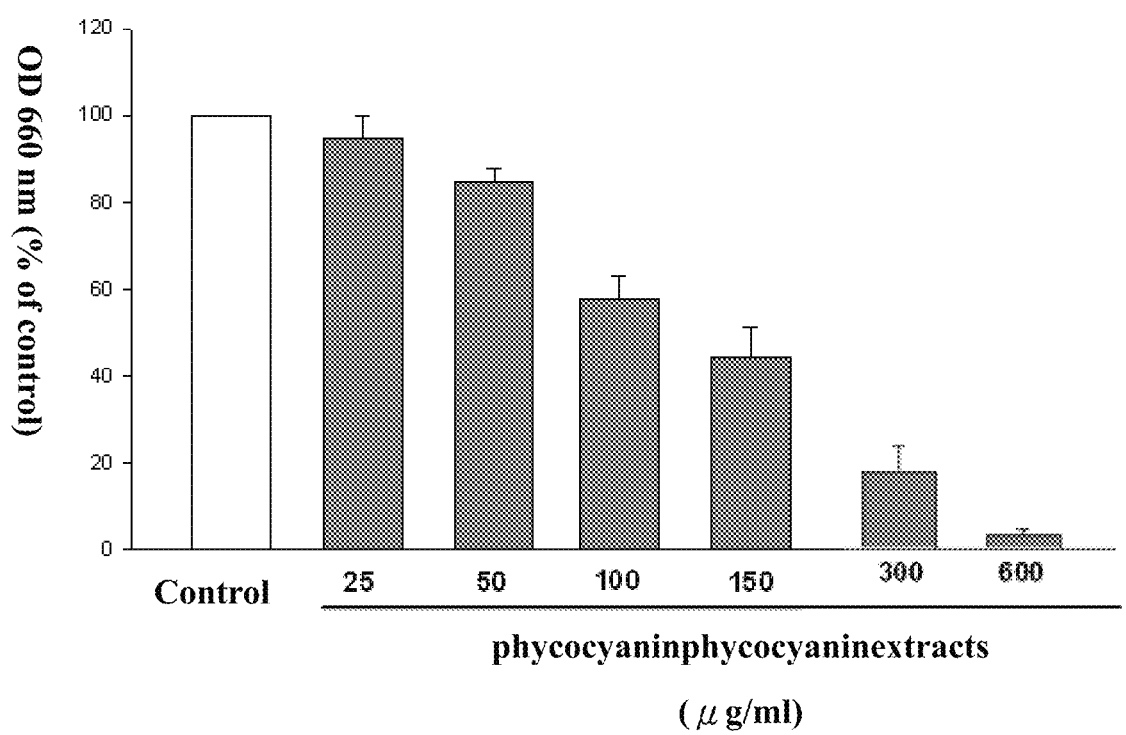
FIG. 1(A) illustrates effect of CPC antimicrobial activity for *Porphyromonas gingivalis* in vitro.
Figure 1B:
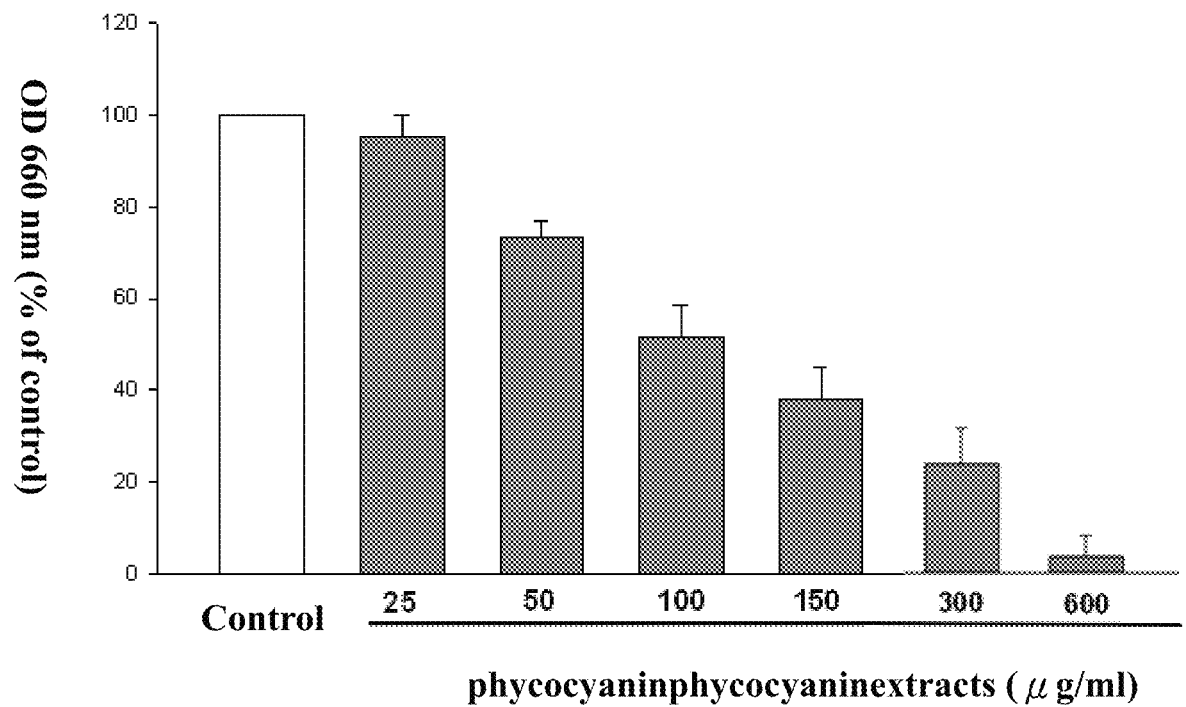
FIG. 1(B) illustrates effect of CPC antimicrobial activity for *Actinobacillus actinomycetemcomitans* in vitro.

To find out the dosage which 50% of bacteria is inhibited, experiment studies the effects of different concentrations of the phycocyanin (25, 50, 150, 300, and 600 μg/ml) on *Porphyromonas gingivalis* (FIG. 1A) and *Actinobacillus actinomycetemcomitans* (FIG. 1B).

The inhibition experiment of the *Porphyromonas gingivalis* (FIG. 1A) indicates that the 50% inhibit concentration of the phycocyanin extracts is about 150 μg/ml. The inhibit experiment of the *Actinobacillus actinomycetemcomitans* results (FIG. 1B) indicate that 50% inhibit concentration of the phycobiliproteins extracts is about 100 μg/ml. But phycocyanin extracts present no inhibitory effect to the other pathogens of the *E. coli, S. aureus, Streptococcus mutans* and *T. rubrum*. These results show the invention containing extracts of phycocyanin has the outstanding effect of inhibiting the growth of periodontal pathogens.

Embodiment 2

The Experiment of the Alveolar Bone Loss

1. Experiment Animal

The present invention uses Sprague Dawley (SD) male rats as experiment animals; each rat weighs about 280-310 g and was purchased from national animal center in the National Defense Medical Center. The breed environment of the SD rat is around the 23-25° C. and the light setting is on between 8:00-20:00 for 12 hours and set off for the remaining 12 hours. The animal room is supplied with ample feed and water. In addition, the room keeps under proper humidity, and a separate filtered air is supplied.

2. The Set Up of Periodontal Disease Animal Model

Figure 2A:
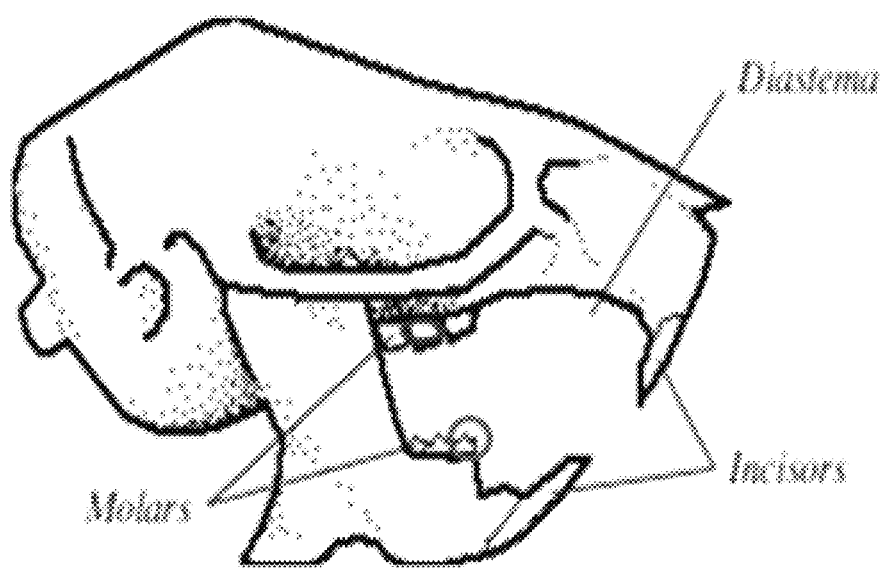
FIG. 2(A) illustrates the chart of the rat dental.
Figure 2B:
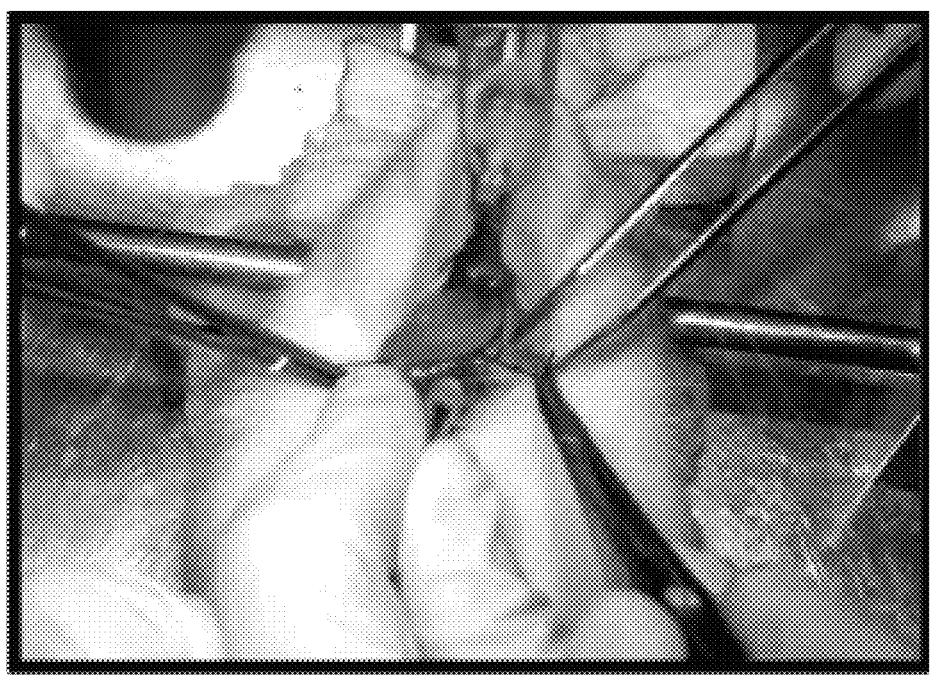
FIG. 2(B) illustrates the operate photograph of the animal induced periodontal experiments.

According to the published paper in 2008 by Cai et al., they setup a Ligature-induced periodontal disease model. (Hereinafter refer to as "ligation"). The first process is to give the rats anesthetic through intraperitoneal injection. Then place the ligature on molars nearby both sides of the jaw around the tooth neck on the primary molar and secondary molar (FIG. 2A and FIG. 2B). The knot is placed at the mesial surface.

3. Experiment Design

Figure 3:
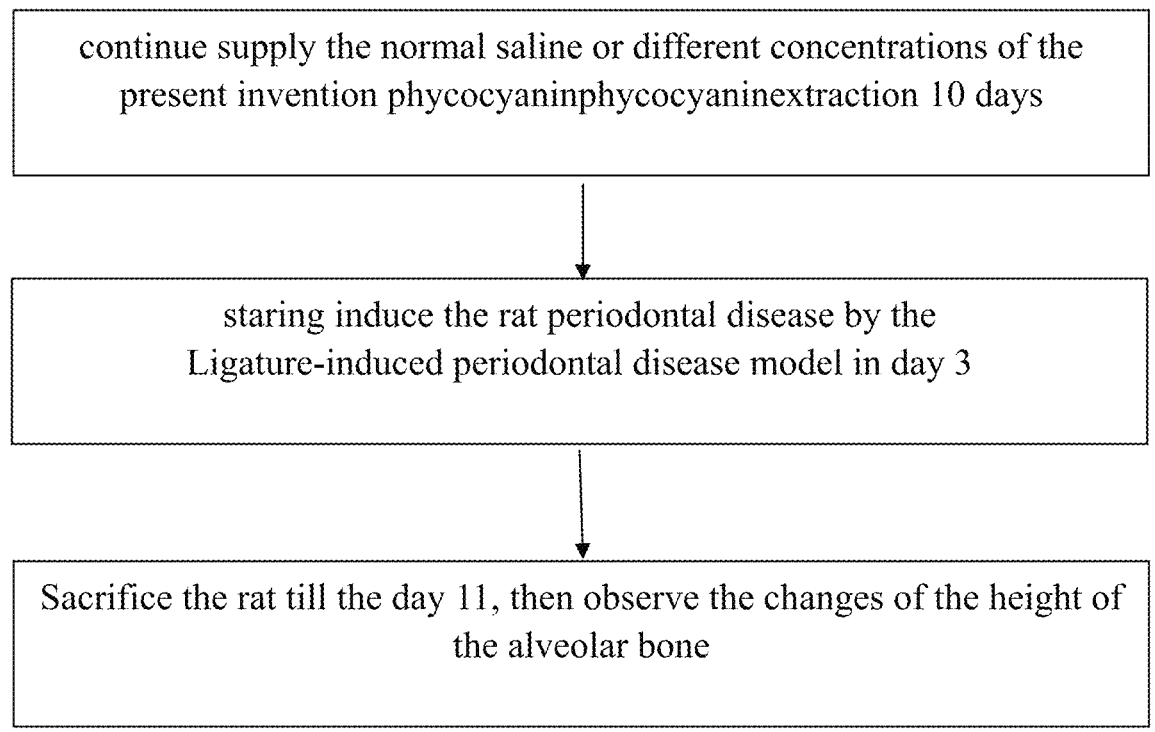
FIG. 3 illustrates the flow chart of animal experiments.

The rats were randomly divided into five groups, include (1) Control group (2) ligation group (3) treatment group 1 (ligation+the phycocyanin extracts 50 mg/kg) (4) treatment group 2 (ligation+the phycocyanin extracts 100 mg/kg) (5) treatment group 3 (ligation+the phycocyanin extracts 200 mg/kg). From the beginning of the experiment D0, normal saline or different concentrations of the present invention contains phycocyanin extraction is given till Day 10. At D3, rat is induced periodontal disease by ligature. Rat are sacrificed at Day 11, and changes of the height of the alveolar bone are observed (FIG. 3)

4. The Measurement of the Height of the Alveolar Bone

Figure 4A:
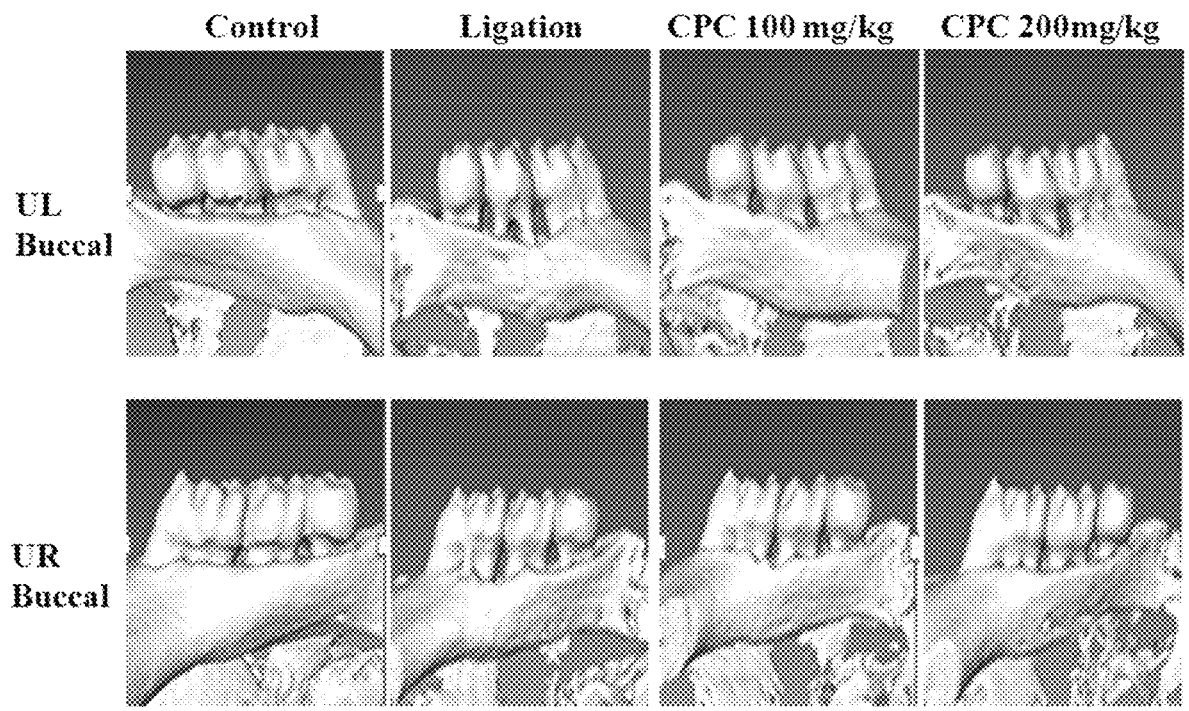
FIG. 4(A) illustrates the MRI photograph of the phenomenon of the alveolar bone loss in animal experiment.
Figure 4B:
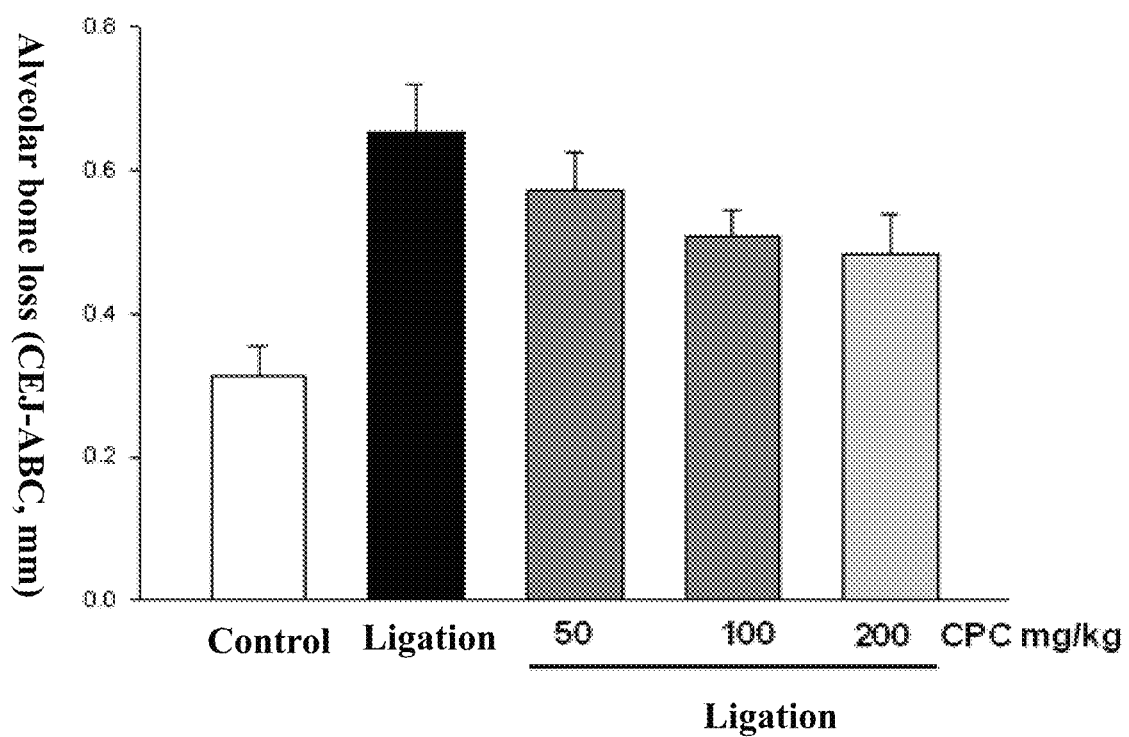
FIG. 4(B) illustrates the statistics result of the alveolar bone loss in animal experiment.
Figure 4C:
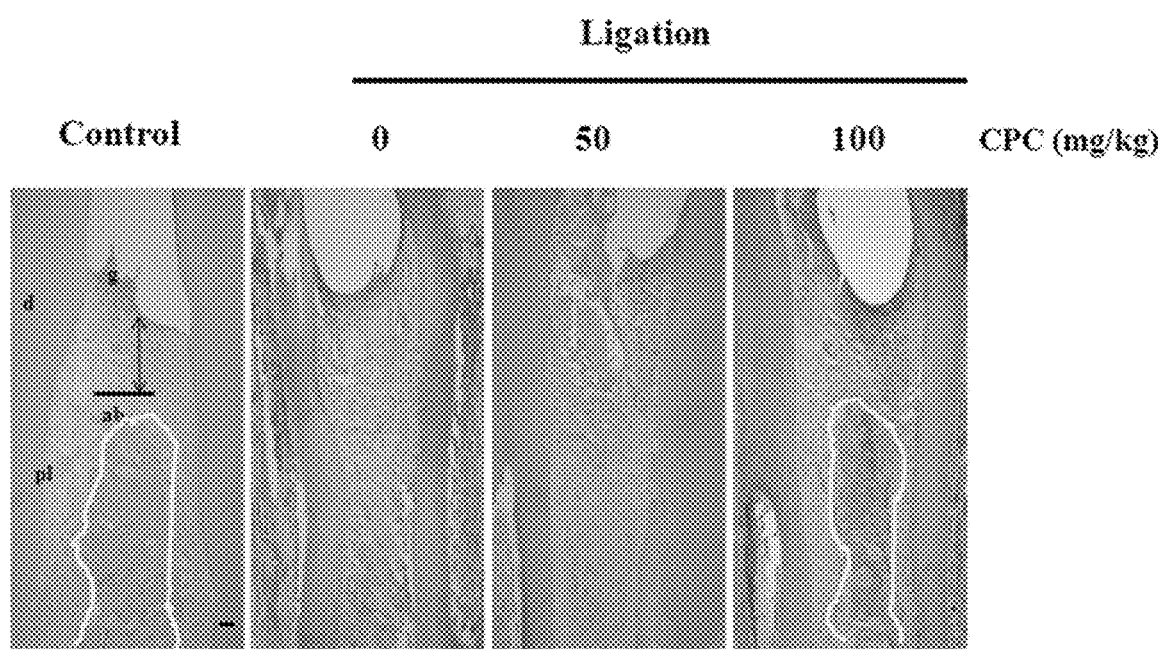
FIG. 4(C) illustrates the photograph of the tissue staining.

After removal of the soft tissues of the rat lower jaw, verify the position of the cemento-enamel junction (CEJ), and measure the distance between the CEJ to the alveolar bone crest (ABC). (FIG. 4A) The experiment result of the Ligation group shows that whether the lingual side or the buccal side the alveolar bone crest both have a serious bone matrix absorption. However, while the rat feed the present invention phycocyanin extraction (C-PC) for 100 mg/kg (treatment group 2) and 200 mg/kg (treatment group 3), the distance between the CEJ to the alveolar bone crest (ABC) is shorter than the Ligation group. (FIG. 4B) There is no difference between the two doses of each other.

Furthermore, observe the experiment rat's alveolar bone loss phenomenon through tissue staining. The mark "d" means dentin, "g" means gingiva, "pl" means periodontal ligament and "ab" means alveolar bone. The experiment result of the Ligation group shows more serious alveolar bone loss than the treatment group. The treatment group 2 (100 mg/kg) and 3 (200 mg/kg) have significant improvement of the alveolar bone loss situation. Therefore, the present invention of the phycocyanin extracts can effectively improve the alveolar bone loss situation.

Based on the above result, the present invention of the phycocyanin extracts can effectively inhibit the growth of the oral pathogens, improve the alveolar bone loss situation and reduce the inflammation caused by those pathogens. Finally, the present invention of the phycocyanin extracts can treatment and/or prevent of periodontal disease.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for inhibiting growth of *Porphyromonas gingivalis* in a subject, the method comprising administering to said subject an effective concentration of a C-phycocyanin in an extract solution,
   wherein the effective concentration is greater than 50 μg/ml in the C-phycocyanin extract solution.

2. A method for inhibiting growth of *Actinobacillus actinomycetemcomitans* in a subject, the method comprising administering to said subject an effective concentration of a C-phycocyanin in an extract solution,
   wherein the effective concentration is greater than 50 μg/ml in a C-phycocyanin extract solution.

3. The method according to claim 1 or 2, wherein the effective concentration is between 50 μg/ml-600 μg/ml in a C-phycocyanin extract solution.

4. The method according to claim 1 or 2, wherein the C-phycocyanin is made into a form selected from the group consisting of a paste, an injection and a patch.

5. The method according to claim 1 or 2, wherein the C-phycocyanin is mixed with a pharmaceutically acceptable excipient.

6. The method according to claim 5, wherein the pharmaceutically acceptable excipient is selected from the group consisting of solvents, dispersion media, coatings, antibacterial agents, antifungal agents, isotonic agents, and absorption delaying agents.

7. The method according to claim 5, wherein the pharmaceutically acceptable excipient is selected from the group consisting of detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

8. The method according to claim 5, wherein the pharmaceutically acceptable excipient is selected from the group consisting of lactose, mannitol, dextran, glucose, glutamic acid, gelatin, sorbitol, trehalose, sucrose, xylitol, starch, microcrystalline cellulose, methyl cellulose, arabic gum and combinations thereof.

9. The method according to claim 1 or 2, wherein the C-phycocyanin is mixed with a food additive.

10. The method according to claim 9, wherein the food additive comprises a sweetener or a potentiator.

11. The method according to claim 9, wherein the food additive is made in the form of a powder, a capsule, or an aqueous alcoholic solution.

12. The method according to claim 9, wherein the food additive is frozen, dried, spray-dried or freeze-dried.

\* \* \* \* \*